United States Patent [19]

Eggler et al.

[11] 4,292,444

[45] Sep. 29, 1981

[54] SULFONYL PROSTAGLANDIN CARBOXAMIDE DERIVATIVES

[75] Inventors: James F. Eggler, Stonington; Thomas K. Schaaf, Old Lyme, both of Conn.

[73] Assignee: Pfizer Inc., New York, N.Y.

[21] Appl. No.: 119,732

[22] Filed: Feb. 8, 1980

[51] Int. Cl.³ .................. C07C 143/74; C07C 177/00
[52] U.S. Cl. ...................................... 564/97; 424/321
[58] Field of Search .................. 260/556 AC; 564/97

[56] References Cited

U.S. PATENT DOCUMENTS 4,098,805  7/1978  Bundy ..................... 260/556 AC X
4,169,895  10/1979  Hess et al. ............... 260/556 AC X

*Primary Examiner*—Arthur P. Demers
*Attorney, Agent, or Firm*—Charles J. Knuth; Peter C. Richardson

[57] ABSTRACT

The synthetic prostaglandin derivatives have a C-1 alkylsulfonylcarboxamide group, a trans C-2, C-3 double bond or cis C-4, C-5 double bond and a C-16 aryloxy group and are antiulcer or antifertility agents.

6 Claims, No Drawings

SULFONYL PROSTAGLANDIN CARBOXAMIDE DERIVATIVES

BACKGROUND

The prostaglandins are C-20 unsaturated fatty acids which exhibit diverse physiological effects. Their structure, nomenclature, biological activities and medicinal use have been described in U.S. Pat. Nos. 3,971,825 and 3,984,400.

A common problem confronting medical scientists who attempt to make biologically efficacious, synthetic drugs is modulation of the biological action of an appropriate lead compound. A traditional approach seeks an increase in biological potency. The prostaglandin approach, however, is framed around increased oral activity and increased duration of action. In addition, enhancement of one of the diverse physiological effects of the prostaglandin class and diminution of the others are sought so that the synthetic prostaglandins will not exhibit incompatible side effects. For example, it would be clinically inadvisable to administer an antiulcer synthetic prostaglandin that also causes diarrhea.

To achieve increased selectivity, efforts have focused on the "active" sites of the natural prostaglandins. In the main, these include the C-1 carboxylic acid group, the cyclopentane ring and the lipophilic end of the bottom side chain. Such work is publicized in the following patents and articles: U.S. Pat. Nos. 4,024,179; 3,954,741; 3,987,087; 3,932,389; 3,054,741; Netherlands Octrooaanvrage No. 7,306,030; G. Traverso et. al., *Il. Farmaco Ed. Sci.* 28, 1040 (1973); C. H. Lin et. al., *Syn. Com.* 6(7)503 (1976); and H. Wakatsuka, *Prostaglandins*, 8, 341 (1974).

SUMMARY

A class of novel sulfonyl prostaglandin carboxamide derivatives has been synthesized and found to have potent, gastric antisecretory and uterine stimulant activity. The class has generic formula I,

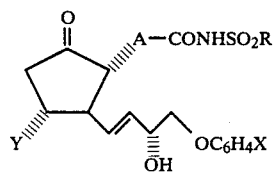

(I)

wherein R is alkyl of 1 to 4 carbons; A is cis $(CH_2)_2HC=CH(CH_2)_2$ or trans $(CH_2)_4CH=CH$; Y is OH or H and X is H, F, Cl, Br, $OCH_3$, $CF_3$ or $CH_3$.

A preferred subclass of derivatives includes those having R as $CH_3$ and X as H.

The preferred embodiments include N-methanesulfonyl 9-oxo-15alpha-hydroxy-16-phenoxy-trans-2-trans-13-omegatetranorprostadienamide of formula I wherein R is $CH_3$, A is trans $(CH_2)_4CH=CH$, Y is H and X is H;

N-methanesulfonyl 9-oxo-11alpha, 15alpha-bishydroxy-16-phenoxy-trans-2-trans-13-omegatetranorprostadienamide of formula I wherein R is $CH_3$, A is trans $(CH_2)_4CH=CH$, Y is OH and X is H;

N-methanesulfonyl 9-oxo-11alpha, 15alpha-bishydroxy-16-phenoxy-cis-4-trans-13-omegatetranorprostadienamide of formula I wherein R is $CH_3$, A is cis $(CH_2)_2CH=CH(CH_2)_2$, Y is OH and X is H; and N-methanesulfonyl 9-oxo-15alpha-16-phenoxy-cis-4-trans-13-omegatetranorprostadienamide of formula I wherein R is $CH_3$, A is cis $(CH_2)_2 CH=CH(CH_2)_2$, Y is H and X is H.

DETAILED DESCRIPTION

The sulfonyl prostaglandin carboxamide derivatives may be synthesized by following the synthetic routes illustrated in Schemes A, B and C below. Scheme A provides the method of formation of the C-2, C-3 trans double bond, Scheme B provides the method of formation of the C-4, C-5 cis double bond and Scheme C provides the method of formation of the alkyl sulfonamide at the C-1 position. The substituents are defined as above and the G substituent is tetrahydropyranyloxy (THPO) or hydrogen.

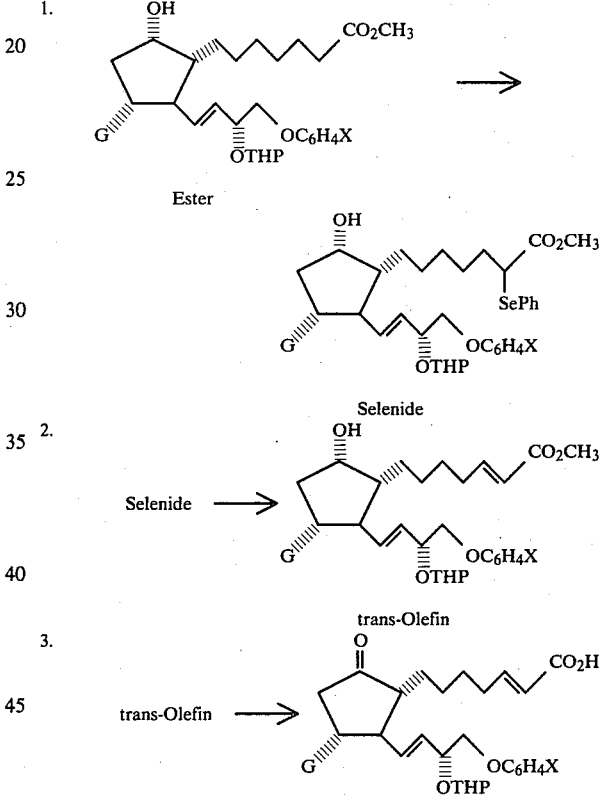

Reactions 1, 2 and 3 of Scheme A constitute the procedure for formation of the C-2, C-3 double bond using the known starting material Ester, 9alpha-hydroxyl-11alpha-(tetrahydropyranyloxy or hydrogen)-15alpha-tetrahydropyranyloxy-16-aryloxy-trans-13-omegatetranorprostenoate.

Reaction 1 is the conversion of Ester to Selenide. First, the Ester carbanion is formed in situ from the Ester by reaction with a strong base such as lithium diisopropylamide in ethereal solvent at $-50°$ to $-75°$. The Selenide is then formed by reaction of the Ester carbanion with diphenyl diselenide.

Reaction 2 is the conversion of Selenide to trans-Olefin. Hydrogen peroxide oxidation and thermal elimination of the resulting phenyl selenoxide group in an ethereal or organic ester solvent will produce the double bond at C-2, C-3.

Reaction 3 is a two step procedure for conversion of the trans-Olefin to the trans-Olefin Acid. Hydrolysis of the C-1 ester group using dilute base in ethereal solvent will produce the C-1 carboxylic acid group. Jones oxidation using Jones reagent ($CrO_3$ and $H_2SO_4$ in acetone) oxidizes the C-9 hydroxyl to a keto group and produces the trans-Olefin Acid.

Reactions 4 through 8 of Scheme B constitute the procedure for formation of the C-4, C-5 double bond using the known starting material Lactone, 2-[3-alpha-(tetrahydroxypyranyloxy or hydrogen)-5alpha-hydroxyl2beta-(3alpha-tetrahydropyranyloxy-4-aryloxy-trans-1-buten-1-yl)cyclopent-1alpha-yl]acetic acid, gamma-lactone.

Reaction 4 is the condensation of the lactone group of the Lactone with 1-dimethyl-t-butylsilyloxy-4-pentynyllithium in ethereal solvent to produce the Ketoyne.

Reaction 5 is the protection of the hydroxyl group at C-9 of the Ketoyne using dimethyl-t-butyl silyl chloride and imidazole in dimethyl formamide.

Reaction 6 is the reduction of the C-7 keto group of the Silated Ketoyne by the three step process involving reduction of the keto group to an alcohol with sodium borohydride in alcohol at ice bath temperature, mesylation of the alcohol group with mesyl chloride in pyridine and reduction of the mesylate with lithium aluminum hydride in ethereal solvent. The product is the Eyne.

Reaction 7 is the Lindlar reduction of the C-4, C-5 triple bond of the Eyne to produce the cis-Olefin. This procedure follows the standard Lindlar method involving catalytic hydrogenation of the triple bond with hydrogen over Lindlar catalyst (Pd-$CaCO_3$-PbO) in a solvent such as ethyl acetate or methanol.

Reaction 8 is a two step procedure converting the cis-Olefin to the cis-Olefin Acid. Removal of the C-1 and C-9 dimethyl-t-butyl silyl protecting groups by reaction with tetra-n-butylammonium fluoride in tetrahydrofuran produces hydroxy groups at these positions. Jones oxidation with Jones reagent ($CrO_3$ and $H_2SO_4$ in acetone) converts these hydroxyl groups to a carboxylic acid group and keto group respectively and accomplishes preparation of the cis-Olefin Acid.

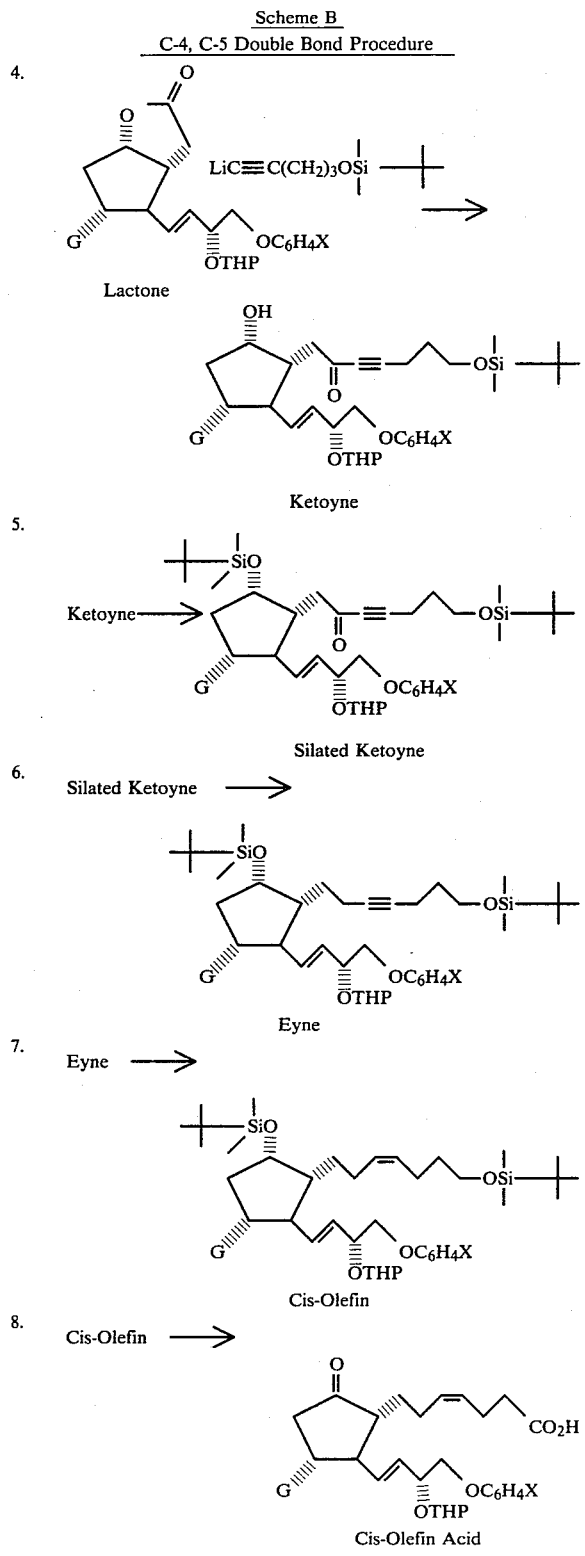

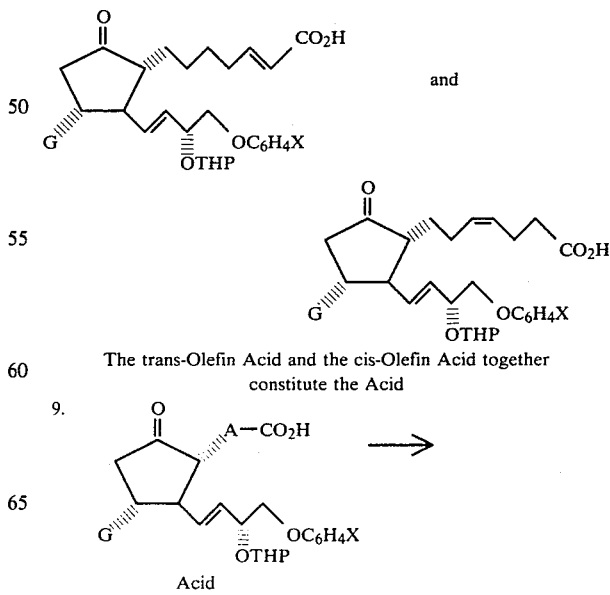

-continued
Scheme C
Preparation of Sulfonamide

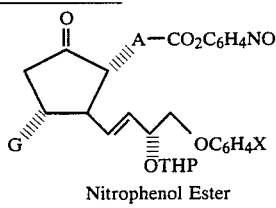
Nitrophenol Ester

10. Nitrophenol Ester ⟶

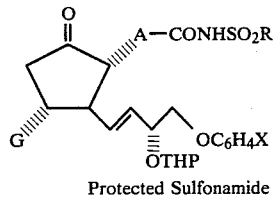
Protected Sulfonamide

11. Protected Sulfonamide ⟶

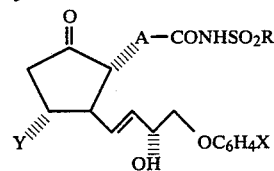

Reactions 9 through 11 of Scheme C constitute the procedure for conversion of the C-1 carboxylic acid group of the trans-Olefin Acid or the cis-Olefin Acid to the N-alkanesulfonyl carboxamide group. This produces the sulfonyl prostaglandin carboxamide derivatives of the invention (Sulfonamide). In Scheme C the trans-Olefin Acid and cis-Olefin Acid are treated equivalently and together are termed Acid.

Reaction 9 is the esterification of the Acid with p-nitrophenyl acetate in pyridine to produce the Nitrophenol Ester.

Reaction 10 is the amidation of the Nitrophenol Ester with an excess of lithium alkylsulfonylamide in tetrahydrofuran at about 30° to 65° for about 0.5 to 15 hours. The Protected Sulfonamide is produced.

Reaction 11 is the deprotection of the 15-tetrahydropyranyloxy group and if appropriate, the 11-tetrahydropyranyloxy group to produce the final product, the Sulfonamide. Hydrolysis with acetic acid in water at about ambient temperature for 6 to 36 hours accomplishes deprotection.

To isolate and purify the intermediates and the sulfonyl prostaglandin carboxamide derivatives produced by reactions 1 through 11, appropriate standard techniques such as extraction, crystallization, chromatography, high pressure liquid chromatography and the like may be used. Analysis of the reaction mixture using techniques such as NMR spectroscopy, IR spectroscopy, thin layer chromatography and the like will reveal whether such purification is necessary. These methods are known to those skilled in the art.

In numerous in vivo and in vitro tests, it is established that the sulfonyl prostaglandin carboxamide derivatives exhibit extreme selectivity. Their biological achievement is the diminution of many of the physiological activities of the natural prostaglandins while maintaining activity in others. The standard tests, known to those skilled in the art and which allow such determination of selectivity, include among others a test for effect on isolated smooth muscle from guinea pig uterus, effect on dog blood pressure, inhibition of histamine induced bronchoconstriction in the guinea pig, inhibition of cold, stress-induced ulceration in the rat, antisecretory activity in the dog and diarrheal effect in the mouse.

After comparison with the responses caused by a natural prostaglandin in the same tests, the pharmacological responses caused by the derivatives in these tests are helpful in determining their usefulness for the treatment of natural and pathological malconditions. Based upon such comparison, the sulfonyl prostaglandin carboxamide derivatives have utility as antiulcer agents and as antifertility agents.

The results of biological tests of N-methanesulfonyl 9-oxo-15alpha-hydroxy-16-phenoxy-trans-2-trans-13-omegatetranorprostadienamide show that it causes substantial inhibition of gastric acid secretion in the pentagastrin stimulated dog and significant smooth muscle response in the guinea pig uterine strip test but little activity in the dog blood pressure test and guinea pig bronchodilator test relative to $PGE_2$.

The derivatives can be used in a variety of pharmaceutical preparations which contain the derivative, or its pharmacologically acceptable salt. They may be administered in the same manner as natural prostaglandins by a variety of appropriate routes, such as intravenous, intraperitoneal, intravaginal and oral among others.

For pharmaceutical preparations and for solid compounding of the derivatives the useful, pharmacologically acceptable salts are those with pharmacologically acceptable metal cations, amine cations, or quaternary ammonium cations.

Especially preferred metal cations are those derived from the alkali metals, e.g., lithium, sodium and potassium, and from the alkaline earth metals, e.g., magnesium and calcium, although cationic forms of other metals, e.g., aluminum, zinc and iron, are within the scope of this invention.

Pharmacologically acceptable amine cations are those derived from primary, secondary or tertiary amines. Examples of suitable amines are methylamine, dimethylamine, triethylamine, ethylamine, benzylamine, alpha-phenylethylamine, beta-phenylethylamine, as well as heterocyclic amines, e.g., piperidine, morpholine, pyrrolidine and piperazine as well as amines containing water-solubilizing or hydrophilic groups, e.g., mono-, di- and tri-ethanolamine, ethyldiethanolamine, galactamine, N-methylglucosamine, ephedrine, phenylephedrine, epinephrine, procaine and the like.

Examples of suitable pharmacologically acceptable quaternary ammonium cations are tetramethylammonium, tetraethylammonium, benzyltrimethylammonium, phenyltriethylammonium and the like.

The derivatives can be used in a variety of pharmaceutical compositions and they may be administered by several routes as described above. Although the particular dose, formulation and route of administration are dependent upon each patient's unique condition and the judgment of his attending physician, the guidelines below present the general treatment regimen.

The derivatives are useful as antiulcer agents. For treatment of peptic ulcers, these drugs are appropriately administered orally in the form of aqueous suspensions, ethanolic solutions or preferably in the form of capsules or tablets containing 0.005 to 0.50 mg/kg of derivative per dose with up to 12 doses per day or may be administered intravenously or intraperitoneally in the form of ethanolic or isotonic sterile solutions containing 0.5 to 50 μg/kg of derivative per dose.

The derivatives are also useful as abortifacient and fertility control agents. To induce abortion, these drugs are appropriately administered orally in the form of aqueous suspensions, ethanolic solutions or preferably in the form of capsules or tablets containing from 0.1 to 10.0 mg of derivative per dose with from 1 to 7 doses per day being employed.

If an intravaginal treatment for abortion induction is desired, a suitable agent is a sterile ethanolic or isotonic solution of the derivative or lactose tablets of the derivative. In such treatments suitable doses are from about 0.5-50 mg of derivative per dose with 1 or 6 doses per day being employed.

In cases where a midterm abortion is necessary, an effective agent is an ethanol-dextrose solution of the derivative administered as an intravenous infusion. A suitable dosage is about 5-500 microgram per minute administered for a period of from about 1 to 48 hours. For extraamniotic, intrauterine administration, ethanol-dextrose solutions of the derivatives are effective agents. A suitable dosage is 0.01 to 10 mg of derivative injected up to 12 times over a 24 hour period.

Another use of the derivative is as an inducer of labor. For this purpose an ethanol-saline solution of the derivative is employed as an intravenous infusion in the amount of from about 3 to 100 microgram of derivative per kilogram patient per minute for from about 1 to 24 hours.

Another use of the derivatives is for fertility control. For this purpose a lactose tablet impregnated with a sterile 95% solution of the derivative is employed for intravaginal administration in the amount of 1-20 mg of derivative per dose with 1 to 6 doses per day being employed 2 to 7 days after the expected day of menstruation had passed.

To prepare any of the above dosage forms or any of the numerous other forms possible, various inert diluents, excipients or carriers may be employed. Such substances include, for example, water, ethanol, gelatins, lactose, starches, magnesium stearate, talc, vegetable oils, benzyl alcohols, gums, polyalkylene glycols, petroleum jelly, cholesterol and other known carriers for medicaments. If desired, these pharmaceutical preparations may contain auxiliary material such as preserving agents, wetting agents, stabilizing agents, or other therapeutic agents such as antibiotics.

The following examples are merely illustrative and in no way limit the scope of the appended claims.

In general, the temperatures of the reactions described in the examples, when unspecified, indicate ambient or room temperature which varies from 15° to 30° C.

The time requirements of the reactions described in the examples, unless otherwise stated, are determined by monitoring with thin layer chromatography (TLC).

EXAMPLE 1

Methyl 2-phenylselenyl-9alpha-hydroxy-15alpha-tetrahydropyranyloxy-16-phenoxy-trans-13-omegatetranorprostenoate (Selenide 1)

Lithium diisopropyl amide was prepared by adding 2.9 ml of 1 M n-butyl lithium in hexane to a solution of 650 mg of diisopropylamine in 20 ml dry tetrahydrofuran (hereinafter called THF) at −75° and stirring for about 15 minutes. To this solution at −75° was then added 1.02 g of methyl-9alpha-hydroxy-15alpha-tetrahydropyranyloxy-16-phenoxy-trans-13-omegatetranorprostenoate (starting material) in 388 mg hexamethylphosphoramide (hereinafter called HMPA). The resulting yellow solution was stirred at −75° for one hour and then 2.02 gm of diphenyldiselenide in 10 ml THF was added. The reaction was stirred at −75° for 30 minutes and then poured into a two phase mixture of 100 ml saturated brine, 100 ml ether. The aqueous layer was extracted three times with 40 ml each of ether and the combined organic layer were dried, filtered and concentrated to produce a yellow oil. Chromatography on silica gel with 10% ethyl acetate in chloroform gave 899 mg of the above titled Selenide 1. NMR (DCCl$_3$): 6.70-7.75 (10H, m C$_6$H$_5$), 5.30-5.68 (2H, m, trans CH=CH), 3.50δ (3H, s, OCH$_3$).

EXAMPLE 2

Methyl 9alpha-hydroxy-15alpha-tetrahydropyranyloxy-16-phenoxy-trans-2-trans-13-omegatetranorprostadienoate (trans-Olefin 2)

To a stirred solution of Selenide 1 (899 mg) in 10 ml THF and 10 ml ethyl acetate (hereinafter called EAC) was added 1.6 ml of 30% hydrogen peroxide and the reaction stirred at ambient temperature for 30 minutes. It was then poured into 30 ml of water and the organic layer extracted three times with 10 ml water, dried with MgSO$_4$, filtered and concentrated to yield an oil. Chromatography on silica gel with chloroform gave 297 mg of the above titled trans-Olefin 2. NMR (DCCl$_3$): 6.70-7.50 (6H, m, C$_6$H$_5$ and C-3 proton), 5.90 (1H, br, C-2 proton), 5.30-5.48 (2H, m, $\Delta^{13,14}$-trans CH=CH), 3.75δ (3H, s, OCH$_3$).

EXAMPLE 3

9-oxo-15alpha-tetrahydropyranyloxy-16-phenoxy-trans-2-trans-13-omegatetranorprostadienoic acid (trans-Olefin Acid 3)

To a solution of 297 mg of trans-Olefin 2 in 3 ml of THF was added 2.0 ml of 1 N aqueous sodium hydroxide. The reaction was stirred at ambient temperature overnight then neutralized with 2.0 ml of 1 N hydrochloric acid. The reaction mixture was extracted three times with 7 ml EAC and the combined organic layers washed with 2 ml brine, dried, filtered and concentrated to yield 265 mg of the 9-hydroxy acid corresponding to trans-Olefin Acid 3 above.

A solution of the above 9-hydroxy acid (0.56 mmoles) and 5 ml acetone was cooled to 0°, Jones reagent (0.56 mmoles) added and the solution was stirred at 0° for 15 minutes. The reaction was poured into 25 ml ether, the organic layer washed with 5 ml water, 5 ml brine, dried and concentrated to give 300 mg of crude product. It was chromatographed on silica gel with chloroform, EAC to yield 200 mg of the pure above titled trans-Olefin Acid 3. NMR (DCCl$_3$): 7.40-6.65 (6H, m, C$_6$H$_5$ and C-3 proton), 6.45 (2H, br, OH), 5.90 (1H, s, C-2 proton), 5.70-5.30δ (2H, m, $\Delta^{13,14}$-trans CH=CH).

EXAMPLE 4 p-Nitrophenyl 9-oxo-15alpha-tetrahydropyranyloxy-16-phenoxy-trans-2-trans-13-omegatetranorprostadienoate (Ester 4)

To the Trans-Olefin Acid 3 (200 mg) in 3 ml of pyridine was added p-nitrophenylacetate (156 mg). The reaction was stirred for 1.5 hours, then diluted with 15 ml ether, washed with 5 ml each of water and brine and the organic layer dried and concentrated to yield 270 mg of the above titled Ester 4. NMR ($DCCl_3$): 8.15 (4H, t, $C_6H_4 NO_2$), 7.65–6.70 (6H, m, $C_6H_3$ and C-3 proton), 5.95 (1H, br, C-2 proton), 5.90–5.60$\delta$ (2H, m, $\Delta^{13,14}$-trans CH=CH).

EXAMPLE 5

N-Methanesulfonyl 9-oxo-15alpha-tetrahydropyranyloxy-16-phenoxy-trans-2-trans-13-omegatetranorprostadienamide (Protected Sulfonamide 5)

To a stirred solution of methyl sulfonylamine (138 mg) in 4 ml THF was added 0.4 ml of n-butyl lithium (2.22 M in hexane). After 10 minutes a solution of the Ester 4 (270 mg) in 3 ml THF was added to the lithium methyl sulfonamide solution. The reaction was stirred at ambient temperature overnight, then heated at 55° for one hour. It was poured into 10 ml water, acidified to pH 3 with acetic acid and the acidified mixture extracted with 50 ml EAC. The organic layer was dried and concentrated to give 340 mg of crude product. Chromatography on silica gel with ether yielded 140 mg of the above titled protected Sulfonamide 5. NMR ($DCCl_3$): 7.40–6.85 (6H, m, $C_6H_5$ and C-3 proton), 3.30$\delta$ (3H, s, $SO_2CH_3$).

EXAMPLE 6

N-Methanesulfonyl 9-oxo-15alpha-hydroxy-16-phenoxytrans-2-trans-13-omegatetranorprostadienamide (Sulfonamide 6)

A solution of protected Sulfonamide 5 (140 mg) and 5 ml of 65:35 acetic acid:water was stirred for 36 hours. The solution was concentrated and the residue chromatographed on silica gel with ether. The chromatographed product was dissolved in 5 ml chloroform, washed with 2 ml water and the organic layer dried and concentrated to yield 60 mg of the above Sulfonamide 6. NMR ($DCCl_3$): 7.60–6.80 (6H, m, $C_6H_5$ and C-3 proton), 6.15–5.70 (3H, m, C-2 proton and $\Delta^{13,14}$-trans CH=CH), 4.60 (1H, m, CHOH), 4.00 (2H, m, $CH_2O$), 3.30$\delta$ (3H, s, $SO_2CH_3$).

The other derivatives of the invention wherein A is trans $(CH_2)_4CH=CH$ may be synthesized using the procedures of Examples 1 through 6 by substituting the appropriate methyl 9alpha-hydroxy-11-(tetrahydropyranyloxy or hydrogen)-15alpha-tetrahydropyranyloxy-16-aryloxy-trans-13-omegatetranorprostenoate for the starting material of Example 1 or the appropriate alkyl sulfonamide for methyl sulfonamide of Example 5.

EXAMPLE 7

1-(dimethyl-t-butylsilyloxy)-6-oxo-9alpha-hydroxy-11alpha,15alpha-bis(tetrahydropyranyloxy)-16-phenoxy-trans-13-omegatetranorprosten-4-yne (Ketoyne 7)

To a solution of 2-[3alpha-tetrahydropyranyloxy-5alpha-hydroxy-2beta-(3alpha-tetrahydropyranyloxy-4-phenoxy-trans-1-buten-1-yl)cyclopent-1alpha-yl]acetic acid, gamma-lactone (starting material 7) (2 mmoles) in 10 ml ether is added 1-dimethyl-t-butyl silyloxy-4-pentynyllithium [4 mmoles, prepared according to the method of C. H. Lin, *Syn. Com.*, 6, 503 (1976)] in 3 ml ether. After stirring for a period sufficient to allow complete reaction, the solution may be quenched with aqueous ammonium chloride and worked up using conventional techniques such as extraction and chromatography to yield the above titled Ketoyne 7.

EXAMPLE 8

1,9alpha-bis(dimethyl-t-butylsilyloxy)-6-oxo-11alpha,15alpha-bis(tetrahydropyranyloxy)-16-phenoxy-trans-13-omegatetranorprosten-4-yne (Silated Ketoyne 8)

The Ketoyne 7 is silated by stirring a mixture of it (3 mmoles), dimethyl-t-butylsilyl chloride (6 mmoles), imidazole (6 mmoles) and dimethyl formamide (hereinafter called DMF) at ambient temperature overnight. Work up by extraction and chromatography will yield the above titled Silated Ketoyne 8.

EXAMPLE 9

1,9alpha-bis(dimethyl-t-butylsilyloxy)-11alpha,15alpha-bis(tetrahydropyranyloxy)-16-phenoxy-trans-13-omegatetranorprosten-4-yne (Eyne 9)

To a solution of the Silated Ketoyne 8 (2 mmoles) in 5 ml absolute methanol at 0° is added sodium borohydride (2 mmoles) in methanol. After stirring at 0° for a period sufficient to provide complete reduction, the reaction may be quenched with water and worked up by extraction. The resulting C-6 hydroxy compound is then dissolved in 3 ml pyridine and mesyl chloride (3 mmoles) added. After stirring for a period sufficient to provide complete reaction, the reaction is concentrated to remove all volatiles. The residue is dissolved in ether, filtered and lithium aluminum hydride (3 mmoles) added to the ethereal solution. After stirring until the reaction is complete, it may be worked up by extraction and chromatography to yield the above titled Eyne 9.

EXAMPLE 10

1,9alpha-bis(dimethyl-t-butylsilyloxy)-11alpha,15alpha-bis(tetrahydropyranyloxy)-16-phenoxy-cis-4-trans-13-omegatetranorprostadiene (cis-Olefin 10)

The Eyne 9 (2 mmoles) is dissolved in 10 ml methanol, Lindlar catalyst (10 mg; Pd, $CaCO_3$, PbO) added and the mixture hydrogenated in an atmospheric hydrogenation apparatus until one equivalent of hydrogen has been taken up. The mixture is then filtered and concentrated to yield the above titled cis-Olefin 10.

EXAMPLE 11

9-oxo-11alpha,15-alpha-bis(tetrahydropyranyloxy)-16-phenoxy-cis-4-trans-13-omegatetranorprostadienoic acid (cis-Olefin Acid 11)

To a solution of cis-Olefin 10 (2 mmoles) in 5 ml THF is added tetra-(n-butyl)ammonium fluoride (8 mmoles) in 3 ml THF. After stirring at ambient temperature until complete, the reaction mixture is partitioned in a mixture of EAC and water and the organic layer dried and concentrated to yield the crude 1,9-dihydroxy compound. This compound is dissolved in 5 ml acetone, cooled to 5° and Jones reagent (6 mmoles $CrO_3$, $H_2SO_4$) added. The reaction is stirred for 15 minutes at 5°, quenched with isopropanol and worked up by extraction and chromatography to yield the above titled cis-Olefin Acid 11.

EXAMPLE 12

N-Methanesulfonyl 9-oxo-11alpha,15alpha-bishydroxy-16-phenoxy-cis-4-trans-13-omegatetranorprostadienamide (Sulfonamide 12)

Following the procedures of Examples 4, 5 and 6, cis-Olefin Acid 11 is converted to Sulfonamide 12 by formation of the p-nitrophenyl ester, reaction of the ester with lithium methanesulfonamide in THF and deprotection of the resulting methane sulfonyl carboxamide in 65:35 acetic acid:water.

The other derivatives of the invention wherein A is cis $(CH_2)_2CH=CH(CH_2)_2$ may be synthesized using the procedures of Examples 7 through 12 by substituting the appropriate 2-[3alpha-(tetrahydropyranyloxy or hydrogen)-5alpha-hydroxy-2beta-(3alpha-tetrahydropyranyloxy-4-aryloxy-trans-1-buten-1-yl)cyclopent-1alpha-yl]acetic acid, gamma-lactone for starting material 7 of Example 7 or the appropriate alkyl sulfonamide for methyl sulfonamide used in Example 12.

We claim:

1. A sulfonyl prostaglandin carboxamide derivative of the formula

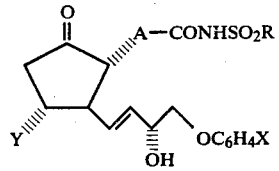

or the pharmacologically acceptable salt thereof, wherein:
 R is alkyl of 1 to 4 carbons;
 A is cis $(CH_2)_2HC=CH(CH_2)_2$ or trans $(CH_2)_4HC=CH$;
 Y is H or OH; and
 X is H, F, Cl, Br, $OCH_3$, $CF_3$ or $CH_3$.

2. A derivative of claim 1 wherein R is $CH_3$ and X is H.

3. The derivative of claim 1 wherein R is $CH_3$, A is trans $(CH_2)_4HC=CH$, Y is H and X is H.

4. The derivative of claim 1 wherein R is $CH_3$, A is trans $(CH_2)_4HC=CH$, Y is OH and X is H.

5. The derivative of claim 1 wherein R is $CH_3$, A is cis $(CH_2)_2HC=CH(CH_2)_2$, Y is OH and X is H.

6. The derivative of claim 1 wherein R is $CH_3$, A is cis $(CH_2)_2HC=CH$ $(CH_2)_2$, Y is H and X is H.

* * * * *